US012655089B2

(12) United States Patent
Wainer

(10) Patent No.: US 12,655,089 B2
(45) Date of Patent: Jun. 16, 2026

(54) HYDROXYNORKETAMINE ANALOGUES, COMPOSITIONS COMPRISING SAME AND METHODS OF USE THEREOF

(71) Applicant: SPIRIFY PHARMA Inc., Saddle Brook, NJ (US)

(72) Inventor: Irving William Wainer, Washington, DC (US)

(73) Assignee: SPIRIFY PHARMA INC., Naples, FL (US)

( * ) Notice: Subject to any disclaimer, the term of this patent is extended or adjusted under 35 U.S.C. 154(b) by 728 days.

(21) Appl. No.: 18/010,249

(22) PCT Filed: Jun. 16, 2021

(86) PCT No.: PCT/IL2021/050732

§ 371 (c)(1),
(2) Date: Dec. 14, 2022

(87) PCT Pub. No.: WO2021/255737

PCT Pub. Date: Dec. 23, 2021

(65) Prior Publication Data

US 2023/0265046 A1 Aug. 24, 2023

Related U.S. Application Data

(60) Provisional application No. 63/040,142, filed on Jun. 17, 2020.

(51) Int. Cl.
*C07C 225/20* (2006.01)
*A61P 31/14* (2006.01)
*C07C 215/44* (2006.01)

(52) U.S. Cl.
CPC ............ *C07C 225/20* (2013.01); *A61P 31/14* (2018.01); *C07C 215/44* (2013.01); *C07C 2601/14* (2017.05)

(58) Field of Classification Search
CPC .................................................... C07C 225/20
See application file for complete search history.

(56) References Cited

U.S. PATENT DOCUMENTS

| | | | |
|---|---|---|---|
| 9,650,352 | B2 | 5/2017 | Wainer et al. |
| 10,683,262 | B2 | 6/2020 | Xiang et al. |
| 2004/0248964 | A1 | 12/2004 | Crooks et al. |
| 2014/0296241 | A1 | 10/2014 | Wainer et al. |
| 2015/0259277 | A1 | 9/2015 | Sleigh et al. |
| 2019/0083420 | A1 | 3/2019 | Wainer et al. |
| 2021/0363109 | A1 | 11/2021 | Wainer |

FOREIGN PATENT DOCUMENTS

| | | | |
|---|---|---|---|
| EP | 0194984 | A1 | 9/1986 |
| WO | 2013056229 | A1 | 4/2013 |
| WO | 2017087388 | A1 | 5/2017 |
| WO | 2018104729 | A1 | 6/2018 |
| WO | 2018234568 | A2 | 12/2018 |
| WO | 2019192602 | A1 | 10/2019 |
| WO | 2019243791 | A1 | 12/2019 |
| WO | 2021234697 | A1 | 11/2021 |
| WO | 2021255737 | A1 | 12/2021 |

OTHER PUBLICATIONS

Han, Y., Mahender Reddy, K., & Corey, E. J. (2017). Simple Enantioselective Syntheses of (2R,6R)-Hydroxynorketamine and Related Potential Rapid-Onset Antidepressants. Organic Letters, 19(19), 5224-5227. doi:10.1021/acs.orglett.7b02498.

European Patent Office, Extended European Search Report for European Patent Application No. 21826067.7, dated Jun. 17, 2024, 9pp.

De Kock, Marc, Sebastien Loix, and Patricia Lavand'homme. "Ketamine and peripheral inflammation." CNS neuroscience & therapeutics 19.6 (2013): 403-410. Retrieved from <https://onlinelibrary.wiley.com/doi/pdf/10.1111/cns.12104>.

Torres, German, et al. "Ketamine intervention limits pathogen expansion in vitro." Pathogens and disease 76.2 (2018):fty006. Retrieved from <https://booksc.org/book/70162835/c037ed>.

Lockhart, Brian Paul, Noel Tordo, and Henri Tsiang. "Inhibition of rabies virus transcription in rat cortical neurons with the dissociative anesthetic ketamine." Antimicrobial agents and chemotherapy 36.8 (1992): 1750-1755. Retrieved from <https://www.ncbi.nlm.nih.gov/pmc/articles/PMC192041/pdf/aac00042-0184.pdf>.

Rantamaki et al. "Antidepressant drug action-From rapid changes on network function to network rewiring" Progress In Neuro-Psychopharmacology & Biological Psychiatry, 2016, vol. 64, pp. 285-292, available online Jun. 9, 2015. https://doi.org/10.1016/j.pnpbp.2015.06.001.

Zanos et al., "Ketamine and Ketamine metabolite pharmacology" Pharmacological Reviews Jul. 1, 2018, 70 (3) 621-660; DOI: https://doi.org/10.1124/pr.117.015198.

K. Hirota, and D. G. Lambert; Ketamine and depression; British Journal of Anaesthesia, 121 (6): 1198e1202 (2018). DOI: 10.1016/j.bja.2018.08.020.

Yukihiko Shirayama, Kenji Hashimoto; Lack of Antidepressant Effects of (2R,6R) Hydroxynorketamine in a Rat Learned Helplessness. Model: Comparison with (R)-Ketamine; International Journal of Neuropsychopharmacology (2018) 21(1): 84-88. doi:10.1093/ijnp/pyx108.

Yanning Li et al., Effects of Ketamine on Levels of Inflammatory Cytokines IL-6, IL-1b, and TNF-a in the Hippocampus of Mice Following Acute or Chronic Administration; Frontiers in Pharmacology; Mar. 2017 | vol. 8 | Article 139. doi: 10.3389/fphar.2017.00139.

Ho MF, Zhang C, Zhang L, Li H, Weinshilboum RM. Ketamine and Active Ketamine Metabolites Regulate STAT3 and the Type I Interferon Pathway in Human Microglia: Molecular Mechanisms Linked to the Antidepressant Effects of Ketamine. Front Pharmacol. 2019;10:1302. Published Nov. 5, 2019. doi:10.3389/fphar.2019.01302.

(Continued)

*Primary Examiner* — Yong S. Chong
(74) *Attorney, Agent, or Firm* — The Roy Gross Law Firm, LLC; Roy D. Gross

(57) ABSTRACT

The present disclosure pertains to amino cyclohexanone compounds, pharmaceutical compositions containing same and methods of treating depression, pain, inflammation, and other clinical indications.

3 Claims, No Drawings

(56) References Cited

OTHER PUBLICATIONS

Singh et al. Ketamine Metabolites Enantioselectively Decrease Intracellular D-Serine Concentrations in PC-12 Cells; PLOS One; Apr. 20, 2016; DOI:10.1371/journal.pone.0149499.
G. Shaked et al.; Ketamine improves survival and suppresses IL-6 and TNFalpha production in a model of Gram-negative bacterial sepsis in rats; Resuscitation 62 (2004) 237-242. doi:10.1016/j.resuscitation.2004.02.015.
Andersson et al. Molecular Medicine (2020) 26:42; Extracellular HMGB1: a therapeutic target in severe pulmonary inflammation including COVID-19 ?. DOI: 10.1186/s10020-020-00172-4.
Brian E Leonard; Inflammation and depression: a causal or coincidental link to the pathophysiology? Acta Neuropsychiatr; Feb. 2018;30(1):1-16. doi: 10.1017/neu.2016.69. Epub Jan. 23, 2017. DOI: 10.1017/neu.2016.69.
Giovanni Amodeo et al.,; Depression and Inflammation: Disentangling a Clear Yet Complex and Multifaceted Link; Neuropsychiatry (London) (2017) 7(4), 448-457. DOI:10.4172/Neuropsychiatry.1000236.
Sota Omoigui; The Biochemical Origin of Pain: The origin of all Pain is Inflammation and the Inflammatory Response. PART 2 of 3—Inflammatory Profile of Pain Syndromes; Med Hypotheses. 2007 ; 69(6): 1169-1178. doi:10.1016/j.mehy.2007.06.033.
Yvonne C. Lee; Effect and Treatment of Chronic Pain in Inflammatory Arthritis; Curr Rheumatol Rep. Jan. 2013 ; 15(1): 300. doi: 10.1007/s11926-012-0300-4.
Zanos et al. NMDAR inhibition-independent antidepressant actions of ketamine metabolites; doi:10.1038/nature17998. Nature vol. 533, pp. 481-486 (2016).
Jeffrey S Kroin, Vaskar Das, Mario Moric and Asokumar Buvanendran; Efficacy of the ketamine metabolite (2R,6R)-hydroxynorketamine in mice models of pain; Kroin JS, et al. Reg Anesth Pain Med 2019;44:111-117. doi: 10.1136/rapm-2018-000013.
Ho, M-F. et al.; Ketamine and Ketamine Metabolites as Novel Estrogen Receptor Ligands: Induction of Cytochrome P450 and AMPA Glutamate Receptor Gene Expression; Biochem Pharmacol. Jun. 2018 ; 152: 279-292. doi:10.1016/.bcp.2018.03.032.
Mehta P. et al. COVID-19: consider cytokine storm syndromes and immunosuppression; vol. 395, Issue 10229, p. 1033-1034, Mar. 28, 2020; The Lancet; DOI:https://doi.org/10.1016/S0140-6736(20)30628-0.
Vashkiv LB, Donlin LT. Regulation of type I interferon responses. Nat Rev Immunol. Jan. 2014;14(1):36-49. doi:10.1038/nri3581. PMID: 24362405; PMCID: PMC4084561.
PCT International Search Report for International Application No. PCT/IL2021/050732, mailed Aug. 25, 2021, 6pp.
PCT Written Opinion for International Application No. PCT/IL2021/050732, mailed Aug. 25, 2021, 8pp.
PCT International Search Report for International Application No. PCT/IL2021/050574, mailed Aug. 9, 2021, 4pp.
PCT Written Opinion for International Application No. PCT/IL2021/050574, mailed Aug. 9, 2021, 7pp.
PCT International Search Report for International Application No. PCT/US2016/062039, mailed Feb. 1, 2017, 3pp.
PCT Written Opinion for International Application No. PCT/US2016/062039, mailed Feb. 1, 2017, 4pp.

HYDROXYNORKETAMINE ANALOGUES, COMPOSITIONS COMPRISING SAME AND METHODS OF USE THEREOF

CROSS REFERENCE TO RELATED APPLICATIONS

This application is a National Phase of PCT Patent Application No. PCT/IL2021/050732, having International filing date of Jun. 16, 2021 which claims the benefit of priority of U.S. Provisional Patent Application No. 63/040,142, filed Jun. 17, 2020, the contents of which are all incorporated herein by reference in their entirety.

FIELD OF THE INVENTION

The present invention pertains to novel hydroxynorketamine (HNK) analogs and uses thereof in the treatment of depression, pain, inflammation, and other clinical indications.

BACKGROUND OF THE INVENTION (R,S)-Ketamine (hereinafter collectively referred to as ketamine) is a phenyl cyclohexylamine derivative consisting of two optical enantiomers, (S)- and (R)-ketamine. Ketamine is an effective anesthetic agent that does not produce significant cardiovascular or pulmonary effects. Sub-anesthetic doses of the drug are widely used as non-opioid analgesic for peripheral pain, neuropathic pain associated with complex regional pain syndrome (CRPS), and migraine headache. It is also prescribed to reduce perioperative opioid usage and in the clinical treatment of depression, suicidal ideation, and post-traumatic stress syndrome (PTSD). The racemic, 50:50 ketamine mixture, i.e., (R,S)-ketamine, is the predominately used formulation, although the FDA has recently approved an intranasal formulation containing (S)-ketamine for use in the treatment of depression. (S)-ketamine is also widely used for pain indications.

(R,S)-Ketamine is rapidly and extensively metabolized into a wide range of N-demethylated, hydroxylated and unsaturated compounds and their respective enantiomeric and diastereomeric isomers. The clinical use of (R,S)-ketamine and (S)-ketamine is limited due to the preferred route of administration (i.e., i.v.) and its dissociative side effects. Further, ketamine is considered an addictive and controlled substance.

U.S. Pat. No. 9,650,352 to an inventor of the present invention discloses pharmaceutical preparations containing (2R,6R)-hydroxynorketamine, or (R)- or (S)-dehydronorketamine, or other stereoisomeric dehydro or hydroxylated ketamine metabolite. The disclosure provides methods of treating bipolar depression, major depressive disorder, neuropathic and chronic pain, including complex regional pain disorder (CRPS) by administering a purified ketamine metabolite or a ketamine metabolite prodrug directly to patients in need of such treatment, the content of which is incorporated herein by reference.

International patent application, publication No. WO/2017/087388 to an inventor of the present invention discloses phenyl cyclohexanone based active agents, pharmaceutical preparations containing such active agents, methods of modifying cellular activity by contacting cells with such active agents, and methods of treating various conditions by administering such active agents to a patient, the content of which is incorporated herein by reference.

International patent application, publication No. WO 2018/104729 is directed to analogs of the ketamine metabolites 6-hydroxyketamine and 6-hydroxynorketamine with applications in the treatment of depression disorders and anxiety disorders.

Recent clinical, animal, and cell-based data suggests that the alterations in the levels of inflammatory cytokines IL-6, IL-1β, and TNF-α may be involved in the neurotoxicity of ketamine (Yanning Li et al., Frontiers in Pharmacology, Volume 8, Article 139). Additional data suggests that ketamine given 5 min or 2 h after induction of *E. coli* sepsis improves survival, possibly by interfering with the inflammatory cascade as evidenced by attenuation of cytokine production (G. Shaked et al., Resuscitation 62 (2004) 237-242).

Further studies demonstrated that the 2-phenylcyclohexanone, hydroxynorketamine (HNK), a rapidly and major metabolite of ketamine, produces many of the therapeutic effects attributed to ketamine in the treatment of depression and neuropathic pain. Both (2R,6R)-HNK and (2S,6S)—HNK are pharmacologically active and do not produce the same degree of dissociative effects attributed to ketamine. HNK isomers are orally bioavailable and exhibit lower toxicity and favorable distribution and elimination profiles. The effect on intracellular and mitochondrial signaling has been determined, and the data indicate that treatment with (2R,6R)-HNK and/or (2S,6S)—HNK produces increased signaling in the mTOR pathway.

Giovanni Amodeo et al., (Neuropsychiatry 2017; Volume 7, Issue 4) studied the link between depression and inflammation. Further, Brian E. Leonard (ACTA NEUROPSYCHIATRICA, Volume 30, Issue 1, February 2018, pp. 1-16) reviews how chronic low-grade inflammation and hypercortisolaemia, which are frequently associated with major depression, contribute to neurodegeneration and how they detrimentally impact on brain energy metabolism.

As to pain, irrespective of the type of pain, whether it is acute or chronic pain, peripheral or central pain, nociceptive or neuropathic pain, a possible origin thereof includes inflammation and the inflammatory response (Sota Omoigui, Med Hypotheses. 2007; 69(6): 1169-1178).

Coronaviruses are a group of related RNA viruses that cause diseases in mammals and birds. In humans, these viruses cause respiratory tract infections that can range from mild to lethal. These are enveloped viruses with a positive-sense single-stranded RNA genome and a nucleocapsid of helical symmetry.

Secondary haemophagocytic lymphohistiocytosis (sHLH) is an under-recognized, hyperinflammatory syndrome characterized by a fulminant and fatal hyper-cytokinemia, causing multi-organ failure. In adults, sHLH is most commonly triggered by viral infections. Cardinal features of sHLH include unremitting fever, cytopenias, and hyperferritinemia. Further, pulmonary involvement, including acute distress syndrome (ARDS), occurs in approximately 50% of patients afflicted with sHLH.

Accumulating data demonstrate a cytokine profile associated with coronavirus disease 2019 (COVID-19) severity, which resembles the profile of sHLH. This cytokine profile is characterized by increased interleukin IL-2, IL-7, granulocyte colony stimulating factor (G-CSF), interferon-γ inducible protein 10 (CXCL10), monocyte chemoattractant protein 1 (MCP-1), macrophage inflammatory protein 1-α (MIP-1α), and tumor necrosis factor-α (TNF-α). Predictors of fatality from a recent retrospective, multicenter study of 150 confirmed COVID-19 cases in Wuhan, China, included elevated ferritin and IL-6 ($p<0.0001$), suggesting that mortality might be due to virally driven hyper-inflammation (Mehta P. et al., the Lancet, Vol. 395, p. 1033-1034).

PCT/IL2021/050574 to some inventors of the present invention discloses compositions and methods for treating inflammation in a subject in need thereof using hydroxynorketamine (HNK), a salt thereof, a stereoisomer thereof, or a combination thereof.

SUMMARY OF THE INVENTION

An aspect of the present invention provides an amino cyclohexanone compound of Formula (I), a pharmaceutically acceptable salt thereof, a stereoisomer thereof, or a combination thereof Formula (I)

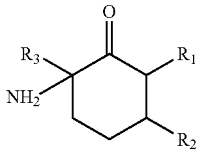

within Formula (I), the variables $R_1$-$R_3$ carry the definitions set forth below:

$R_1$ is —H, —OH, —$N_3$, —$SR_4$, —$SO_2R_4$, —$NHR_4$, or —$N(R_4R_5)$;

$R_2$ is —H, —CN, —$N_3$, —$SR_4$, —$SO_2R_4$, —$NHR_4$, or —$N(R_4R_5)$, wherein $R_4$ and $R_5$ are independently selected from $C_1$-$C_8$ saturated or unsaturated alkyl;

wherein when $R_1$ is —OH, $R_2$ is H, and $R_3$ is

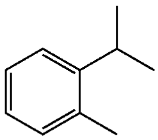 or 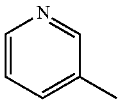

wherein when $R_1$ is —$N_3$, —$SR_4$, —$SO_2R_4$, —$NHR_4$, or —$N(R_4R_5)$, $R_2$ is —H, and $R_3$ is

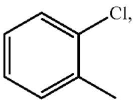, or 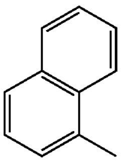

wherein when $R_1$ is —H, $R_2$ is —CN, —$N_3$, —$SR_4$, —$SO_2R_4$, —$NHR_4$, or —$N(R_4R_5)$; and R3 is

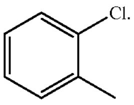.

In yet another aspect, the present invention provides a pharmaceutical composition comprising a compound of Formula I, a pharmaceutically acceptable salt thereof, a stereoisomer thereof, or a combination thereof, and a pharmaceutically acceptable carrier.

In yet another aspect, the present invention provides a method of inhibiting N-methyl-D-aspartate (NMDA) receptor activity comprising contacting cells with an effective amount of a compound of Formula I, a pharmaceutically acceptable salt thereof, a stereoisomer thereof, or a combination thereof. In one or more embodiment, the NMDA receptor's activity is inhibited directly via a direct binding of the herein compounds thereto. In one or more embodiment, the NMDA receptor's activity is inhibited indirectly through other proteins that participate in the signaling cascade of NMDA receptor.

In yet another aspect, the present invention provides a method of modifying endogenous concentrations of D-Serine comprising contacting cells with an effective amount of a compound of Formula I, a pharmaceutically acceptable salt thereof, a stereoisomer thereof, or a combination thereof.

In yet another aspect, the present invention provides a method of stimulating the phosphorylation of mammalian target of rapamycin (mTOR) comprising contacting cells with an effective amount of a compound of Formula I, a pharmaceutically acceptable salt thereof, a stereoisomer thereof, or a combination thereof.

In yet another aspect, the present invention provides a method of inhibiting nAChR activity comprising contacting cells with an effective amount of a compound of Formula I, a pharmaceutically acceptable salt thereof, a stereoisomer thereof, or a combination thereof.

In yet another aspect, the present invention provides a method of inhibiting serine racemase (SR) activity comprising contacting cells with an effective amount of a compound of Formula I, a pharmaceutically acceptable salt thereof, a stereoisomer thereof, or a combination thereof.

In yet another aspect, the present invention provides a method of inhibiting or attenuating the secretion of proinflammatory agents from immune cells comprising contacting the immune cells with an effective amount of a compound of Formula I, a pharmaceutically acceptable salt thereof, a stereoisomer thereof, or a combination thereof.

In one or more embodiments, the proinflammatory agents are selected from a group consisting of IL-6, TNF-$\alpha$, IL-8, IL-1$\beta$, PGE2, and a combination thereof.

In yet another aspect, the present invention provides a method of treating a disease or condition selected from the group consisting of a mental disorder, Alzheimer's dementia, amyotrophic lateral sclerosis, inflammation, and pain, comprising administering a composition comprising a compound of Formula I, a pharmaceutically acceptable salt thereof, a stereoisomer thereof, or a combination thereof, to a subject in need of such treatment.

In yet another aspect, the present invention provides a pharmaceutical composition comprising a compound of Formula I, a pharmaceutically acceptable salt thereof, a stereoisomer thereof, or a combination thereof, for use in the treatment of a disease or condition selected from the group consisting of a mental disorder, Alzheimer's dementia, amyotrophic lateral sclerosis, inflammation, and pain.

In one or more embodiments, the mental disorder is selected from the group consisting of bipolar depression, major depressive disorder, persistent depressive disorder, psychotic depression, suicidality, premenstrual dysphoric disorder (PMDD), atypical depression, post partum depression, obsessive compulsive disorder, post-traumatic stress disorder, and schizophrenia.

In one or more embodiments, the pain is selected from the group consisting of complex regional pain syndrome (CRPS), chronic pain, severe pain, migraine, rheumatic pain, menstrual pain, or neuropathic pain.

In one or more embodiments, the inflammation is caused by a pathogen, a trauma, a hazardous substance, or an autoimmune disease.

In one or more embodiments, the pathogen is selected from the group consisting of a virus, a bacteria, a protozoa, a prion, a viroid, or a fungus.

In one or more embodiments, the pathogen is a virus.

In one or more embodiments, the virus is a SARS-CoV-2.

In one or more embodiments, the inflammation is a hyper-inflammation.

In one or more embodiments, the subject is a mammal.

In one or more embodiments, the subject is a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention pertains to novel amino cyclohexanone compounds and to the use thereof in the treatment of depression, pain (e.g., neuropathic pain), and inflammation.

(2R,6R)-HNK is a pharmacologically active molecule that exerts therapeutic effect via interaction with several possible receptors, including α-amino-3-hydroxy-5-methyl-4-isoxazolepropionic acid (AMPA) receptor and nicotinic acetylcholine receptor. (2R,6R)-HNK interacts with its receptor(s) through hydrogen bonding and hydrophobic interactions.

The herein inventor devised novel HNK analogs to optimize the pharmacological use and efficacy thereof in the treatment of depression, neuropathic conditions, and inflammation and minimize common side effects associated with ketamine administration.

Illustrative examples of active agents in accordance with the present disclosure include the following compounds, stereoisomers, and enantiomers thereof:

Formula (I)

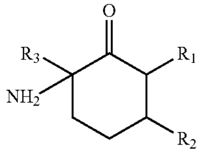

within Formula (I), the variables $R_1$-$R_3$ carry the definitions set forth below:

$R_1$ is —OH, —$N_3$, —$SR_4$, —$SO_2R_4$, —$NHR_4$, or —$N(R_4R_5)$, wherein $R_4$ and $R_5$ are independently selected from $C_1$-$C_8$ saturated or unsaturated alkyl;

$R_2$ is H;

when $R_1$ is —OH, $R_3$ is

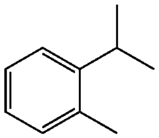

or

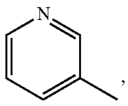

, when $R_1$ is —$N_3$, —$SR_4$, —$SO_2R_4$, —$NHR_4$, or —$N(R_4R_5)$ $R_3$ is

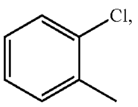

or

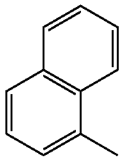

.

$R_1$ may be for example, —$SCH_3$, —$SO_2CH_3$, —$NHCH_3$, or —$N(CH_3)_2$;

The disclosure includes all stereoisomers of compounds of Formula I.

Illustrative examples of active agents in accordance with the present disclosure include the following compounds of Formulas (II) to (XI):

Formula (II)

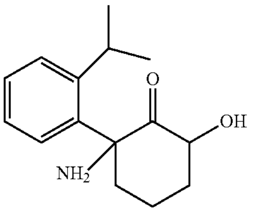

Formula (III)

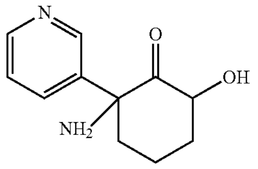

Formula (IV)

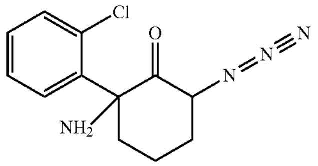

Formula (V)

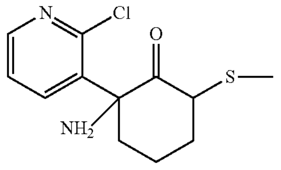

Formula (VI)

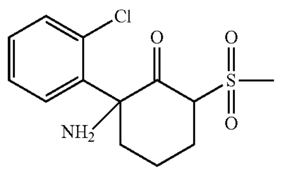

-continued

Formula (VII)

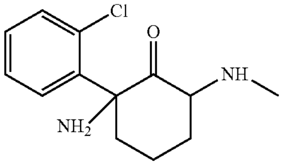

Formula (VIII)

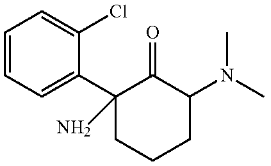

Formula (IX)

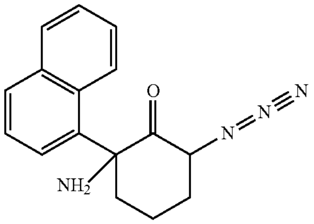

Formula (X)

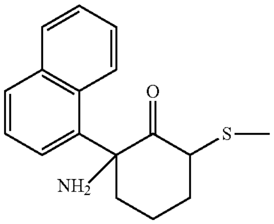

Formula (XI)

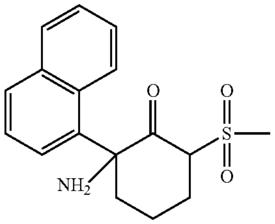

Formula (XII)

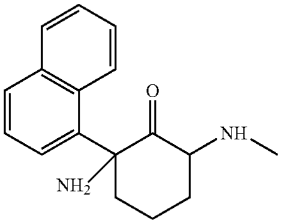

Formula (XIII)

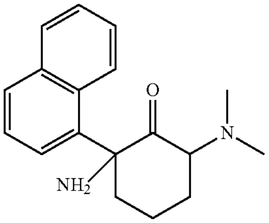

Further illustrative examples of active agents in accordance with the present disclosure include the following compounds, stereoisomers, and enantiomers thereof:

Formula (I)

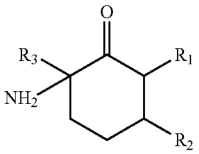

within Formula (I), the variables $R_1$-$R_3$ carry the definitions set forth below:

$R_1$ is H;

$R_2$ is —CN, —$N_3$, —$SR_4$, —$SO_2R_4$, —$NHR_4$, or —$N(R_4R_5)$, wherein $R_4$ and $R_5$ are independently selected from $C_1$-$C_8$ saturated or unsaturated alkyl;

$R_3$ is

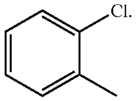

$R_2$ may be, for example, —$SCH_3$, —$SO_2CH_3$, —$NHCH_3$, or $N(CH_3)_2$.

The disclosure includes all stereoisomers of compounds of Formula I. Illustrative examples of active agents in accordance with the present disclosure include the following compounds of Formula (XIV)—(XIX):

Formula (XIV)

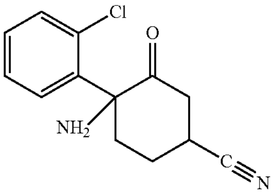

Formula (XV)

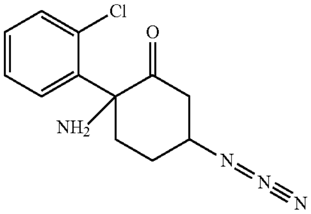

Formula (XVI)

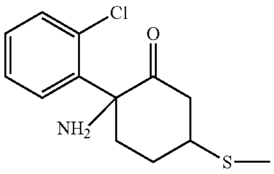

Formula (XVII)

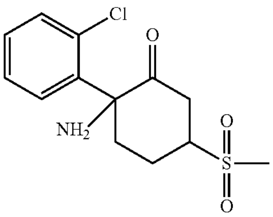

-continued

Formula (XVIII)

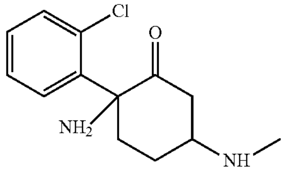

Formula (XIX)

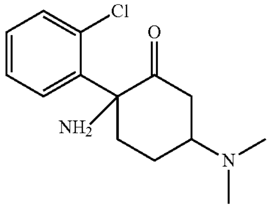

Without being bound by any theory or mechanism of action, the herein compounds, according to Formula I, exert a biochemical effect by a mechanism including one or more of: inhibiting/blocking the N-methyl-D-aspartate NMDA receptor, inhibiting serine racemase (SR) enzyme activity, activating mTOR signaling pathway, activating α-amino-3-hydroxy-5-methyl-4-isoxazolepropionic acid (AMPA) receptor, and inhibiting/blocking nicotinic acetylcholine receptors (nAChR), such as α7 nAChR and α3β4 nAChR. Optionally, administration of the herein disclosed compounds results in a reduction in the intracellular and/or extracellular concentrations of D-serine, a co-agonist of NMDA receptor.

Optionally, an enhanced efficacy is attributed to an enhanced hydrogen bond donating-accepting property of a substituent at the C2 and/or C5, and/or C6 position on the cyclohexanone ring of the herein compounds according to Formula I. The ability of (2R,6R)-HNK to achieve hydrogen bonding interactions is derived from the $NH_2$ substituent at C2 and the OH substituent at C6 of the molecule. Both moieties can act as hydrogen bond donors/acceptors. Also, the ability of (2R,6R)-HNK to interact with a hydrophobic cleft or site on the respective receptor(s) and/or enzyme(s) is thought to be based upon the presence of the 2-cholorbenzyl moiety at the C2 position of the molecule. The C2 and C6 carbons in the (2R,6R)-HNK cyclohexanone ring are asymmetric, and the R stereochemical configuration at both sites may contribute to the observed pharmacological activity of the compound. The present compounds are devised to optimize the pharmacological use and efficacy of (2R,6R)-HNK through enhanced hydrogen bond donor/acceptor strength, steric and three-dimensional configurations of the molecules.

The disclosure also includes compounds and salts of Formula I in which the variables $R_1$-$R_3$ carry the following definitions:

$R_1$ is —H, —OH, —$N_3$, —$SR_4$, —$SO_2R_4$, —$NHR_4$, or —$N(R_4R_5)$, $R_2$ is —H, —CN, —$N_3$, —$SR_4$, —$SO_2R_4$, —$NHR_4$, or —$N(R_4R_5)$, and $R_3$ is

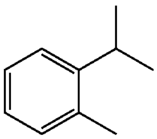
,
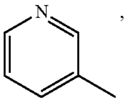
,
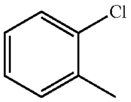
or

-continued

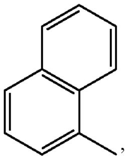
, $R_4$ and $R_5$ are independently selected from $C_1$-$C_8$ saturated or unsaturated alkyl;

when $R_1$ is —OH, —$N_3$, —$SR_4$, —$SO_2R_4$, —$NHR_4$, or —$N(R_4R_5)$, $R_2$ is —H;

when $R_2$ is —CN, —$N_3$, —$SR_4$, —$SO_2R_4$, —$NHR_4$, or —$N(R_4R_5)$, $R_1$ is —H; and when $R_1$ is —OH, $R_3$ is not

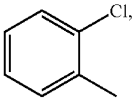
, or
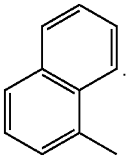
.

Pharmaceutical Compositions

Compounds disclosed herein can be administered as the neat chemical, but in certain embodiments, are administered as a pharmaceutical composition. Accordingly, the disclosure provides pharmaceutical compositions including a compound or pharmaceutically acceptable salt of a compound according to Formula I, together with at least one pharmaceutically acceptable carrier. The pharmaceutical composition may contain a compound or salt of any one of Formulas I-XIX as the only active agent. Still, in some embodiments, the composition contains at least one additional active agent.

The term "carrier" applied to pharmaceutical compositions of the invention refers to a diluent, excipient, or vehicle with which the herein compound or salt of Formulas I-XIX is administered.

Carriers include excipients and diluents and preferably be of sufficiently high purity and sufficiently low toxicity to render them suitable for administration to the patient being treated. The carrier may be inert, or it may possess pharmaceutical benefits of its own. The amount of carrier employed in conjunction with the herein compound is sufficient to provide a practical quantity of material for administration per unit dose of the compound.

Classes of carriers include but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class; for example, vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which does not substantially interfere with the activity of the active agents in accordance with this disclosure.

"Pharmaceutically acceptable salts" are derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric, and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

Methods of Treatment

In an embodiment of the invention, the herein compounds, according to Formula I, and exemplary Formulas II-XIX are effective in treating central nervous system (CNS) or mental or neurological disorders/conditions/diseases, such as bipolar depression, major depressive disorder, schizophrenia, Alzheimer's dementia, amyotrophic lateral sclerosis, and pain (e.g., complex regional pain syndrome (CRPS), chronic pain, severe pain, migraines, menstrual pain, neuropathic pain, or neuropathic pain).

The herein methods of treatment comprise administering to a subject in need of such treatment, a pharmaceutical composition comprising a therapeutic effective amount of the herein disclosed compounds according to Formula I. Specific exemplary compounds include compounds II-XIX.

Accumulating evidence suggests that some patients with severe COVID-19 might experience hyper-inflammation expressed by robust cytokine release (a.k.a., cytokine storm syndrome) or secondary hemophagocytic lymphohistiocytosis (sHLH).

International patent application No.: PCT/IL2021/050574 to an inventor of the present invention discloses an anti-inflammatory efficacy of HNK. Specifically, HNK was demonstrated to inhibit pro-inflammatory agents release (e.g., IL-6, TNF-$\alpha$, IL-8, IL-1$\beta$, PGE2) from monocytes cells stimulated by lipopolysaccharide (LPS), the content of which is incorporated by reference.

Thus, the present invention pertaining to HNK analogs further discloses the use of such analogs in the treatment and management of inflammation and particularly in treating subjects afflicted with an infectious disease associated with hyper-inflammation, such as COVID-19.

Thus, in an embodiment of the invention, the herein compounds, according to Formula I, are further effective in treating subjects afflicted with an infectious disease. In an embodiment of the invention, the herein compounds, according to Formula I, are further effective in treating inflammation. In an embodiment of the invention, the herein compounds, according to Formula I, are further effective in treating inflammation in subjects afflicted with an infectious disease. In an embodiment of the invention, the herein compounds, according to Formula I, are further effective in treating subjects afflicted with a viral disease associated with inflammation. In an embodiment of the invention, the herein compounds, according to Formula I, are effective in the treatment of subjects afflicted with a coronavirus. In an embodiment of the invention, the herein compounds, according to Formula I, are effective in the treatment of subjects afflicted with a SARS-CoV-2. Optionally, the inflammation is a hyper-inflammation.

As used herein the terms "inhibiting or attenuating" includes but is not limited to any one or more of the following: abrogating, ameliorating, blocking, suppressing, reducing, delaying, halting, alleviating or preventing a certain medical effect (e.g., inhibiting the proinflammatory agents secretion from cells).

In an embodiment of the invention, the herein compounds, according to Formula, I are also useful in the treatment of conditions associated with both pain and inflammation, including, but not limited to, musculoskeletal conditions, such as arthritis, sports injury, low back pain, menstrual pain, a systemic inflammation, such as autoimmune disease, pericarditis, and pleuritis.

In an embodiment of the invention, the herein compounds, according to Formula I, are also useful in treating conditions associated with both depression and inflammation, including, but not limited to, chronic arthritis, chronic bowel inflammatory disease, and post major surgery.

As used herein the term "inflammation" refers to a biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and initiate tissue repair. The herein "inflammation" also encompasses inflammatory conditions considered as "hyper-inflammation".

As used herein, the term "hyper-inflammation" refers to syndromes, disorders or conditions caused by severe and uncontrolled immune cell activation and hypercytokinemia (a.k.a., cytokine storm). The clinical presentation of hyper-inflammation inter-alia includes unremitting fever, splenomegaly, coagulopathy, hepatitis, cytopenia, and, if unrestrained, multi-organ failure and death.

Various physiological conditions may be associated with hyper-inflammation. Non-limited examples of conditions associated with an acute inflammatory response include trauma, hazardous substances, microbial invasion, hemophagocytic lymphohistiocytosis (HLH), macrophage activation syndrome, sepsis and cytokine release syndrome. Further, non-limited examples of conditions associated with chronic inflammation include autoimmune diseases (e.g., inflammatory bowel disease, psoriasis, etc.).

As used herein, the term "Cytokine Storm" encompasses a multi-factorial hyper-inflammation associated, inter-alia, with increased expression of one or more of interleukins (IL), chemokines, granulocyte colony-stimulating stimulating factors (G-CSF), and tumor necrosis factor-1$\alpha$ (TNF).

Thus, an aspect of the invention provides a method of treating a viral infection in a subject in need thereof, the method comprising administering to the subject a therapeutic effective amount of the herein compounds according to Formula I.

In an embodiment of the invention, the method comprising identifying inflammation/hyper-inflammation in the subject and treating the hyper-inflammation comprising administering to the subject a therapeutic effective amount of the herein compound(s) according to Formula I.

Identifying inflammation/hyper-inflammation may include assessment of inflammatory markers in a biological sample of a subject, including assessment of increased levels of proinflammatory agents, such as cytokines and chemokines (e.g., the interleukins IL-1b, IL-6, and IL-8, and tumor necrosis factor-1α), C reactive protein (CRP), growth factors (e.g., granulocyte colony-stimulating stimulating factors (G-CSF) and ferritin), and prostaglandins (e.g., PGE2).

Inflammation/hyper-inflammation can be diagnosed using laboratory methodologies. Non-limited examples of suitable laboratory methodologies include ferritin assessment, platelet count assessment, erythrocyte sedimentation rate determination to identify the subgroup of patients for whom immunosuppression treatment could be effective.

The herein compounds may be further used to attenuate proinflammatory agent release or secretion from immune cells Immune cells may include neutrophils, eosinophils, basophils, mast cells, monocytes, macrophages, dendritic cells, natural killer cells, and lymphocytes (B cells and T cells). Additional cell types involved in the immune system may be contemplated, such as astrocytes that are crucial regulators of innate and adaptive immune responses in the injured central nervous system. In one embodiment, the immune cells are monocytes. In one embodiment, the immune cells are macrophages. Optionally the immune cells are stimulated/triggered to secrete proinflammatory cytokines by a pathogen, a.k.a., an infectious agent (e.g., Lipopolysaccharides; LPS). The immune cells may be stimulated by a virus, a bacteria, a protozoan, a prion, a viroid, or a fungus. The immune cells may be stimulated, for example, due to an injury, a trauma, an autoimmune disease, a hazardous substance.

Optionality, a compound(s) as herein disclosed, according to Formula I, will be administered as a single agent or in combination with other drugs including, for example beta2-adrenergic receptor agonists (e.g., metaproterenol, terbutaline, salbutamol, salmeterol, (R,R')-4'-methoxy-1-naphthylfenoterol); GPR55 receptor antagonists (e.g., cannabidiol, (R,R')-4'-methoxy-1-naphthylfenoterol), High-mobility group box 1 (HMGB1) protein inhibitors (e.g., heparin and ascorbic acid); Janus kinase (JAK) inhibitors (e.g., tofacitinib, bracicitinib).

Optionally, a compound(s), as herein disclosed, according to Formula I, may additionally include treatment with steroids, intravenous immunoglobulin, selective cytokine blockade (e.g., anakinra or tocilizumab), and JAK inhibition.

Optionally, a compound, as herein disclosed, according to Formula I, is used in combination with antimicrobials agents, such as antiviral/antiretroviral agents and antibacterial agents, to thereby manage the symptoms of infections, superinfections, and hyper-inflammation.

Exemplary antiviral/antiretroviral agents include, without limitation, agents that inhibit viral replication cycle (e.g., agents that inhibit viral DNA polymerase), agents that inhibit viral cell penetration and/or protein synthesis. In an embodiment of the invention, the antiviral/retroviral agent is effective in treating coronavirus infections (e.g., anti-coronavirus antibodies, stem cell-based treatments, etc.).

Antibacterial agents are typically capable of reducing the metabolic activity of bacteria such that their pathogenic effect in the biological environment will be minimized or eliminated. Exemplary antibiotics include, without limitation, β-Lactam antibiotics (penicillins, cephalosporins, carbapenems, monobactams), Tetracyclines (e.g., doxycycline, minocycline), macrolide antibiotics, aminoglycosides, peptide antibiotics, lincosamides, and streptogramins.

In an embodiment of the invention, the method comprising identifying patient anxiety and depression associated with hospitalization and social distancing due to SARS-CoV-2 infection using the Hospital Anxiety and Depression Scale (HADS) and treating the anxiety and depression by administering a therapeutic effective amount of a compound (s) according to Formula I.

As used herein, the term “coronavirus” refers to a family of various viruses, including, without limitation, severe acute respiratory syndrome (SARS) coronavirus (SARS-CoV), middle east respiratory syndrome coronavirus (MERS) coronavirus (MERS-CoV), and SARS-CoV-2 (that causes COVID-19).

The term “therapeutically effective amount” refers to an amount of the active pharmaceutical agent (herein a compound according to Formula I) effective in the treatment of a disease or disorder in a mammal.

As used herein the term “subject” means any human or non-human animal in need of medical treatment. In some embodiments, the subject is a mammal. In some embodiments, the subject is a human. The term “subject” is interchangeable with the term “patient”.

As used herein the term “prodrug” refers to a medication or compound that, after administration, is metabolized (i.e., converted within the body) into a pharmacologically active drug. Inactive prodrugs are pharmacologically inactive medications that are metabolized into an active form within the body.

Methods of treatment in accordance with the present disclosure include administering a compound of Formula I or any combination of compounds of Formula II-XIX.

Administration of the herein compounds according to Formula I may be before, at the onset of, or following the detection of symptoms (e.g., hyper-inflammation, depression, pain) in the subject.

Compounds disclosed herein may be administered orally, intravenously, intraperitoneally, topically, parenterally, by inhalation or spray, sublingually, transdermal, via buccal administration, rectally, as an ophthalmic solution, or by other means, in dosage unit formulations containing conventional pharmaceutically acceptable carriers.

The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose. The dosage form may provide immediate release, sustained release, or a combination thereof. Gastro-retentive, intramuscular, subcutaneous, and intraocular dosage forms are also contemplated.

Methods of treatment in accordance with the present disclosure include methods of treating bipolar depression, major depressive disorder, schizophrenia, Alzheimer's dementia, amyotrophic lateral sclerosis, complex regional pain syndrome (CRPS), chronic pain, or neuropathic pain and/or inflammation by administering a pharmaceutical composition containing an effective amount of a compound of Formula I or a pharmaceutically acceptable salt thereof, together with a pharmaceutically acceptable carrier to a patient in need of such treatment.

The compound or salt of Formula I may be the only active agent administered or may be administered together with an additional active agent. For example, the compound of Formula I may be administered together with another active agent.

Exemplary active agents include, for example, an anti-depressants, such as, escitalopram, fluoxetine, paroxetine, duloxetine, sertraline, citalopram, bupropion, venlafaxine, duloxetine, naltrexone, mirtazapine, venlafaxine, atomoxetine, bupropion, doxepin, amitriptyline, clomipramine, nortriptyline, buspirone, aripiprazole, clozapine, loxapine, olanzapine, quetiapine, risperidone, ziprasidone, carbamazepine, gabapentin, lamotrigine, phenyloin, pregabalin, donepezil, galantamine, memantine, rivastigmine, tramiprosate, or pharmaceutically active salts or prodrugs thereof, or a combination thereof.

Schizophrenia Medications, include, for example, aripiprazole, lurasidone, asenapine, clozapine, ziprasidone, risperidone, quetiapine, stelazine, olanzapine, loxapine, flupentioxol, perphenazine, haloperidol, chlorpromazine, fluphenazine, prolixin, or paliperidone; Alzheimer's Dementia Medications, such as, for example, donepezil, rivastigmine, galantamine, or memantine.

ALS Medications, include, for example, riluzole; Pain Medications, such as, for example, acetaminophen, aspirin, NSAIDS, including Diclofenac, Diflunisal, Etodolac, Fenoprofen, Flurbiprofen, Ibuprofen, Indomethacin.

Definitions

Compounds disclosed herein are described using standard nomenclature. Unless defined otherwise, all technical and scientific terms used herein have the same meaning as is commonly understood by one of skill in the art to which this disclosure pertains.

The terms "a" and "an" do not denote a limitation of quantity but rather denote the presence of at least one of the referenced items.

The term "chiral" refers to molecules having the property of non-superimposability of the minor image partner.

"Stereoisomers" are compounds having identical chemical constitution but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high-resolution analytical procedures such as electrophoresis, crystallization in the presence of a resolving agent, or chromatography, using, for example, a chiral UPLC column.

"Enantiomers" refer to two stereoisomers of a compound which are non-superimposable mirror images of one another.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

Where a compound exists in various tautomeric forms, the disclosure is not limited to any one of the specific tautomers, but rather includes all tautomeric forms.

The disclosure includes compounds of Formula I having all possible isotopes of atoms occurring in the compounds. Isotopes include those atoms having the same atomic number but different mass numbers. By way of general example, and without limitation, isotopes of hydrogen include tritium and deuterium.

Certain compounds are described herein using a general formula that includes variables, e.g., $R_1$, and $R_2$. Unless otherwise specified, each variable within Formula I is defined independently of other variables. Thus, if a group is said to be substituted, e.g., with 0-2 R*, then said group may be substituted with up to two R* groups, and R* at each occurrence is selected independently from the definition of R*. Also, combinations of substituents and/or variables are permissible only if such combinations result in stable compounds.

The term "substituted" as used herein means that at least one hydrogen on the designated atom or group is replaced with a selection from the indicated group, provided that the designated atom's normal valence is not exceeded. When the substituent is oxo (i.e., =0), then 2 hydrogens on the atom are replaced. When aromatic moieties are substituted by an oxo group, the aromatic ring is replaced by the corresponding partially unsaturated ring. For example, a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, $—(CH_2)$C3-C7 cycloalkyl is attached through carbon of the methylene ($CH_2$) group.

The term "consisting essentially of" means that the composition, or method may include additional ingredients, steps and/or parts, but only if the additional ingredients, steps and/or parts do not materially alter the basic and novel characteristics of the claimed composition, or method.

The term "consisting of" means including and limited to.

As used herein the term "about" refers to ±10% or ±5%.

The terms "comprise", "comprising", "includes", "including", "having" and their conjugates mean "including but not limited to".

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

The invention will be described in detail by way of specific examples. The following examples are offered for illustrative purposes and are not intended to limit the invention in any manner. Those of skill in the art will readily recognize a variety of non-critical parameters, which can be changed or modified to yield essentially the same results. In one or more embodiments, the amounts in the examples should be read with the prefix "about".

Methods of Preparing the Present Compounds

Synthesis of racemic mixture of intermediate 1:

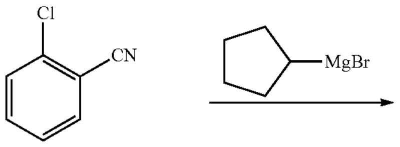

Chemical Formula: $C_7H_4ClN$
Molecular Weight: 137.57

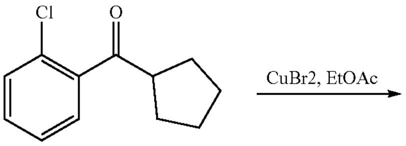

Chemical Formula: $C_{12}H_{13}ClO$
Molecular Weight: 208.69

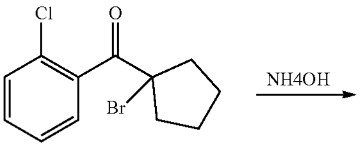

Chemical Formula: $C_{12}H_{12}BrClO$
Molecular Weight: 287.58

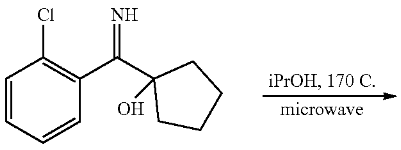

Chemical Formula: $C_{12}H_{14}ClNO$
Molecular Weight: 223.70

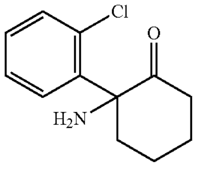

Chemical Formula: $C_{12}H_{14}ClNO$
Molecular Weight: 223.70
Intermediate 1

The following step is the chiral resolution with L-pyroglutamic acid to provide each enantiomer for further transformation and introduction of —OH group in positions 6 and 5 (4-6 step synthesis).

For the molecules with 2,6 substitutions, the inversion of the configuration in position 6 (Mistsunobu type transformation):

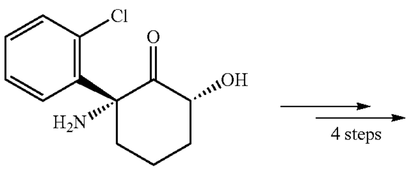

Chemical Formula: $C_{12}H_{14}ClNO_2$
Molecular Weight: 239.70

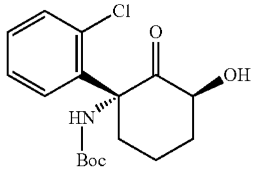

Chemical Formula: $C_{17}H_{22}ClNO_4$
Molecular Weight: 339.82

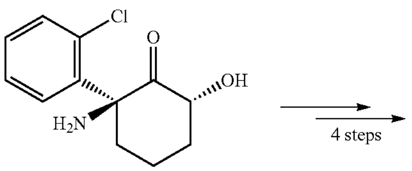

Chemical Formula: $C_{12}H_{14}ClNO_2$
Molecular Weight: 239.70

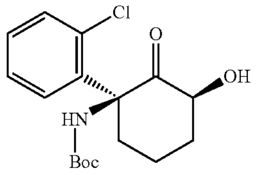

Chemical Formula: $C_{17}H_{22}ClNO_4$
Molecular Weight: 339.82

For the molecules with 2,5 substitutions, the stereoselective epoxidation followed by epoxide ring-opening is conducted.

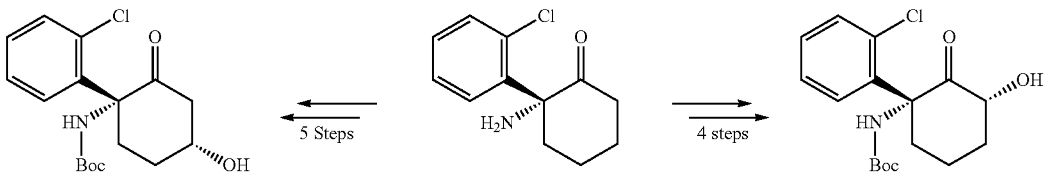

Chemical Formula: $C_{17}H_{22}ClNO_4$
Molecular Weight: 339.82

Chemical Formula: $C_{12}H_{14}ClNO$
Molecular Weight: 223.70

Chemical Formula: $C_{17}H_{22}ClNO_4$
Molecular Weight: 339.82

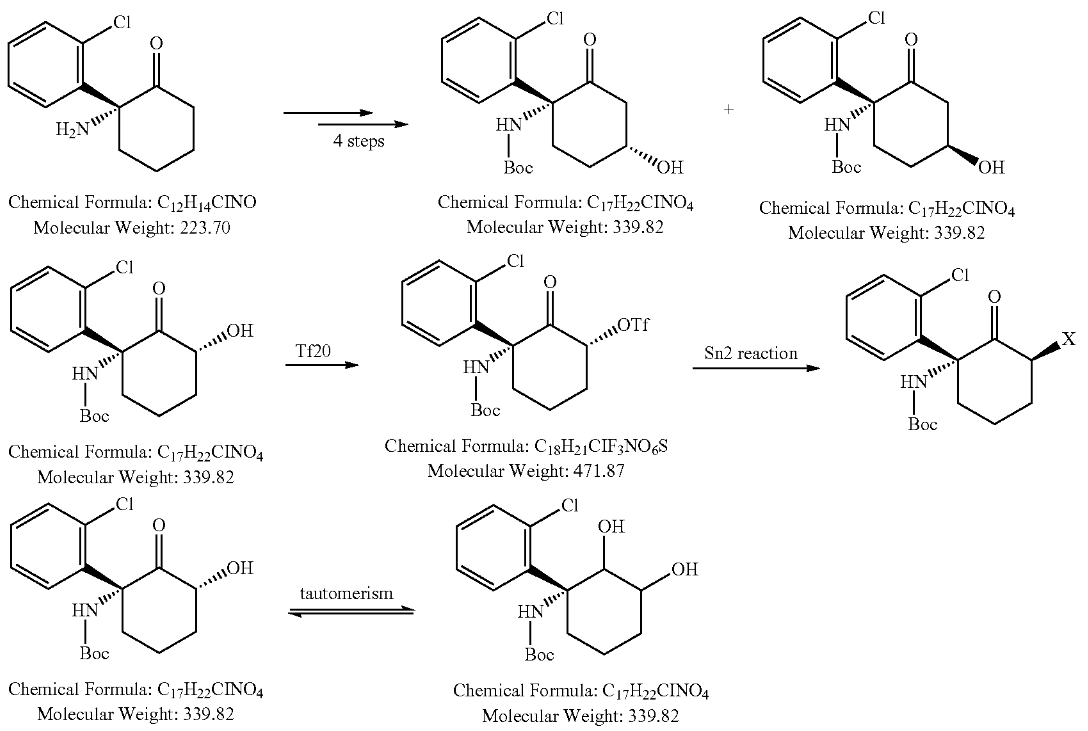

Similar derivatization process can be performed to obtain the derivatives of $R_2$. Products of the herein synthesis are characterized and analyzed by commonly known spectroscopic methods (e.g., H1-NMR, C13-NMR, m.p., IR, Mass-spec).

Determination of D-Serine Concentrations

PC-12 cell line (derived from rat adrenal medulla cells) are seeded on 100x20 mm tissue culture plates and maintained at 37° C. under humidified 5% $CO_2$ in air until they reach >70% confluence. The cells are then incubated for 36 h with media containing the test compounds. The medium is removed, and the cells are assessed for intracellular and extracellular D-serine levels, and expression of serine racemase (SR). All analyses may be repeated in three independent cell cultures (n=3).

Intracellular D-serine concentrations are measured using capillary electrophoresis-laser induced fluorescence (CE-LIF) method using a P/ACE MDQ system equipped with a laser-induced fluorescence detector (Singh et al., Anal Biochem 2012; 421: 460-466). The extracellular D-serine levels are determined by employing liquid chromatography with mass spectrometric detection (Singh et al., Br J Pharmacol 2015; 172: 4546-59).

The expression of mSR and dSR in PC-12 cells may be determined using western blotting (Singh et al., Anesthesiology 2014; 121: 149-59). The primary antibody for d-SR may be obtained from Santa Cruz Biotechnology (Dallas, TX, USA), and the antibody that recognizes both mSR and dSR may be purchased from Abeam, Inc. (Cambridge, MA). The primary antibody for β-actin is from Abeam. Immune reactive bands may be detected using the ECL Plus Western. Blotting Detection System (GE Healthcare, Piscataway, NJ, USA) and quantification may be accomplished by volume densitometry using ImageJ software (National Institutes of Health, Bethesda, MD) and normalization to β-actin.

Measurement of Cytokines Release from Primary Human Monocytes

Human primary monocytes are isolated (enriched) from buffy coats of healthy human blood donors. Cells are seeded in 24-well-plates for ELISA experiments. The results are normalized to LPS, provided as 100%, and presented as percentage of change cytokine levels. The various respective statistical significances are calculated by T-Test. The toxicity of the compounds on the cells is also tested using Alamar Blue. Treatment with toxic amounts of sodium fluoride (NaF at 250 μg/ml) are used as control.

Treatment of SARS-CoV-2 Positive Patients with the Herein Compounds

SARS-CoV-2 positive patients (typically, but not necessarily mild to severe patients) are evaluated for the presence of elevated plasma and/or saliva concentrations of pro-inflammatory agents (e.g., interleukins (IL), chemokines, granulocyte colony-stimulating stimulating factors (G-CSF), and/or tumor necrosis factor-α (TNF-α)), and optionally also other markers of systemic inflammation.

The patient's temperature, blood oxygen levels, respiration rate and other determinants of clinical status are determined. Patient anxiety and depression may be further assessed using the Hospital Anxiety and Depression Scale (HADS).

A pharmaceutical composition comprising one or more compounds according to Formula I-XIX is administered to the patient (optionally in a daily administration), and the plasma or saliva concentrations of the inflammatory markers, general clinical status, and anxiety and depression are monitored. A positive response is defined as reduced plasma/saliva concentrations of the pro-inflammatory agents, improved clinical status, and reduced anxiety and depression as measured by the HADS score. The pharmaceutical composition comprising one or more compounds according to Formula I-XIX may be administered via i.v. infusion, i.p. (intraperitoneal) administration, by intranasal, sublingual, or by oral administration, at an optional dose, below the normal anesthetic dose (e.g., 0.15 mg/kg-0.3 mg/kg, based on total body weight for maximum 20 mg every 6 hours).

While the present invention has been particularly described, persons skilled in the art will appreciate that many variations and modifications can be made. Therefore, the invention is not to be construed as restricted to the particularly described embodiments, rather the scope, spirit, and concept of the invention will be more readily understood by reference to the claims which follow.

What is claimed is:

1. An amino cyclohexanone compound of Formula (I), a stereoisomer, or a pharmaceutically acceptable salt thereof Formula (I)

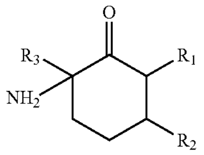

$R_1$ is —H, —OH, —$N_3$, —$SR_4$, —$SO_2R_4$, —$NHR_4$, or —$N(R_4R_5)$;

$R_2$ is —H, —CN, —$N_3$, —$SR_4$, —$SO_2R_4$, —$NHR_4$, or —$N(R_4R_5)$;

wherein $R_4$ and $R_5$ are independently selected from $C_1$-$C_8$ saturated or unsaturated alkyl;

when $R_1$ is —OH, $R_2$ is —H, and $R_3$ is

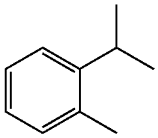

or

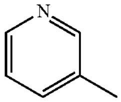

;

when $R_1$ is —$N_3$, —$SR_4$, —$SO_2R_4$, —$NHR_4$, or —$N(R_4R_5)$, $R_2$ is —H, and $R_3$ is

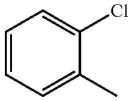

or

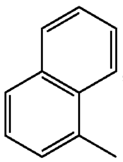

;

when $R_1$ is —H, $R_2$ is —CN, —$N_3$, —$SR_4$, —$SO_2R_4$, —$NHR_4$, or —$N(R_4R_5)$; and $R_3$ is

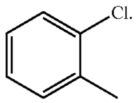

2. An amino cyclohexanone compound as claimed in claim 1, or a pharmaceutically acceptable salt thereof selected from the group consisting of Formula (II) to (XIX):

Formula (II)

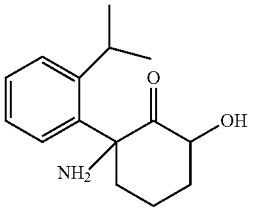

-continued

Formula (III)

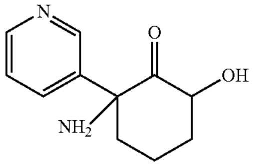

Formula (IV)

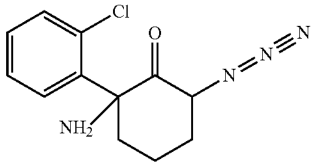

Formula (V)

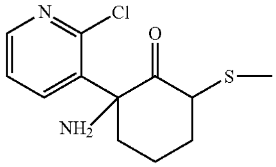

Formula (VI)

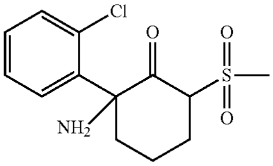

Formula (VII)

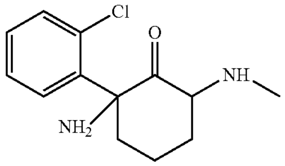

Formula (VIII)

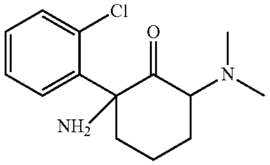

Formula (IX)

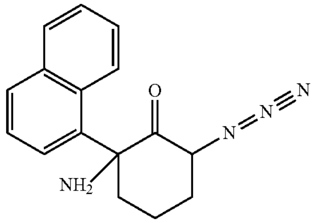

Formula (X)

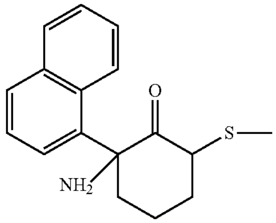

-continued
Formula (XI)
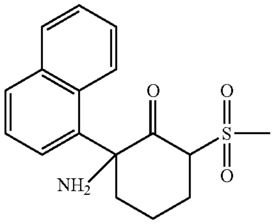
Formula (XII)
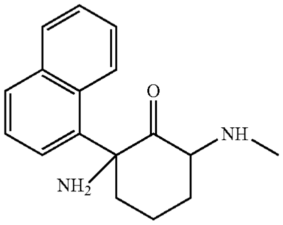
Formula (XIII)
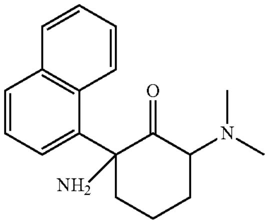
Formula (XIV)
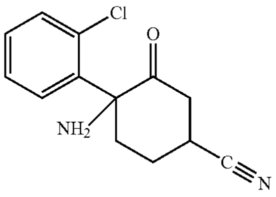
Formula (XV)
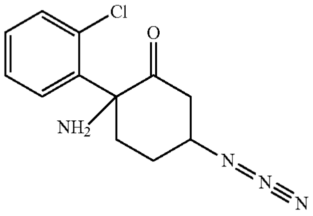
-continued
Formula (XVI)
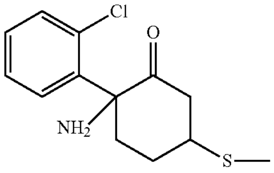
Formula (XVII)
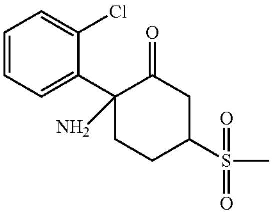
Formula (XVIII)
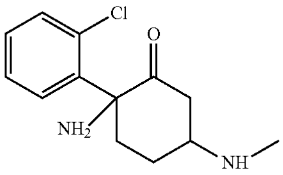
Formula (XIX)
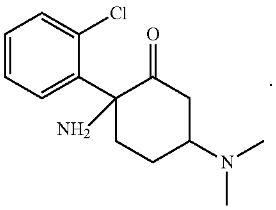
.
3. A pharmaceutical composition comprising an effective amount of a compound according to claim 1, and a pharmaceutically acceptable carrier.
* * * * *